United States Patent [19]
Findeisen et al.

[11] Patent Number: 5,861,358
[45] Date of Patent: *Jan. 19, 1999

[54] SUBSTITUTED SULPHONYLAMINO-CARBONYLTRIAZOLINONES AND THEIR USE AS HERBICIDES

[75] Inventors: Kurt Findeisen; Karl-Heinz Linker, both of Leverkusen; Ernst-Rudolf Gesing, Erkrath-Hochdahl; Joachin Kluth, Langenfeld; Klaus-Helmut Müller, Düsseldorf; Hans-Jochem Riebel, Wuppertal; Klaus König, Odenthal; Hans-Joachim Santel; Markus Dollinger, both of Leverkusen, all of Germany

[73] Assignee: Bayer Aktiengesellschaft, Leverkusen, Germany

[*] Notice: The term of this patent shall not extend beyond the expiration date of Pat. No. 5,552,369.

[21] Appl. No.: 718,326

[22] PCT Filed: Mar. 27, 1995

[86] PCT No.: PCT/EP95/01149

§ 371 Date: Sep. 30, 1996

§ 102(e) Date: Sep. 30, 1996

[87] PCT Pub. No.: WO95/27703

PCT Pub. Date: Oct. 19, 1995

[30] Foreign Application Priority Data

Apr. 7, 1994 [DE] Germany ............... 44 11 913.5

[51] Int. Cl.$^6$ ............ A01N 47/38; C07D 249/12
[52] U.S. Cl. .......... 504/273; 548/263.2; 548/263.4; 548/263.8; 548/264.4
[58] Field of Search ............ 504/273; 548/263.2, 548/263.4, 263.8, 264.4

[56] References Cited

U.S. PATENT DOCUMENTS 5,057,144 10/1991 Daum et al. .................... 71/92
5,552,369 9/1996 Findeisen et al. ............... 504/273

FOREIGN PATENT DOCUMENTS

| 422469 | 4/1991 | European Pat. Off. . |
| 4234801 | 4/1994 | Germany . |
| 9324482 | 5/1993 | WIPO . |

*Primary Examiner*—Patricia L. Morris
*Attorney, Agent, or Firm*—Sprung Kramer Schaefer & Briscoe

[57] ABSTRACT

The invention relates to novel substituted sulphonylamino-cabonyltriazolinones of the formula (I), in which Q represents oxygen, sulphur or the grouping —N($R^4$)—, $R^3$ represents aryl or arylalkyl which are in each case substituted at least twice, with one of the substituents being different from alkyl, and $R^1$, $R^2$ and $R^4$ represent hydrogen or different substituents and also to salts of compounds of the formula (I), to processes for preparing the novel compounds and to their use as herbicides.

7 Claims, No Drawings

SUBSTITUTED SULPHONYLAMINO-CARBONYLTRIAZOLINONES AND THEIR USE AS HERBICIDES

The invention relates to novel substituted sulphonylaminocarbonyltriazolinones, to several processes for their preparation and to their use as herbicides.

It is already known tat certain sulphonylaminocarbonyltriazolinones, such as 4,5-dinethyl-2-(2-chloro-phenylphonyl-aminocarbonyl)-2,4-dihydro-3H-1,2,4-triazol-3-one, exhibit herbicidal properties (cf. EP-A 341 489; cf also EP-A 422 469; EP-A 425 948; EP-A 431 291). However, the effect of these compounds is not satisfactory in all respects.

The novel sulphonylamiocarbonyltriazolinones of the general formula (I), $$R^3-Q-SO_2-NH-CO-N\underset{N}{\overset{}{\diagdown}}\overset{O}{\overset{\|}{C}}\diagup N-R^1 \diagdown\!\!=\!\!\diagup R^2 \quad (I)$$

in which

Q represents oxygen, sulphur or the grouping $-N(R^4)-$, $R^1$ represents hydrogen, hydroxyl, amino or alkylidenamino, or represents a radical, which is in each case optionally substituted, from the group alkyl, alkenyl, alkinyl, cycloalkyl, aralkyl, aryl, alkoxy, alkenyloxy, alkylamino, cycloalkylamino, dialkylamino and alkanoylamino, $R^2$ represents hydrogen, hydroxyl, mercapto, amino or halogen, or represents a radical, which is in each case optionally substituted, from the group alkyl, cycloalkyl, alkenyl, cycloalkenyl, aralkyl, aryl, alkoxy, alkenyloxy, alkinyloxy, cycloalkyloxy, aryloxy, aralkyloxy, alkylthio, alkylsulphinyl, alkylsulphonyl, alkenylthio, alkinylthio, cycloalkylthio, arylthio, aralkylthio, alkylamino, alkenylamino, arylamino, aralkylamino, dialkylamino, aziridino, pyrrolidino, piperidino and morpholino, $R^3$ represents aryl or arylalkyl which are in each case substituted at least twice, where one of the substituents is different from alkyl, $R^4$ represents hydrogen, hydroxyl, amino, cyano or alkoxycarbonyl, represents optionally substituted alkyl, alkenyl, alkinyl, alkoxy, alkenyloxy, aralkoxy, aryloxy or dialkoxy(thio)phosphoryl, or represents the following grouping $Q^1-R^5$, in which $Q^1$ represents $-CO-$ or $-SO_2-$, and $R^5$ represents alkyl, cycloalkyl or aryl which are in each case optionally substituted, and salts of compounds of the formula (I) have now been found The novel sulphonylaminocarbonyltriazolinones of the formula (I) are obtained if (a) chlorosulphonylaminocarbonyltriazolinones of the general formula (II)

$$Cl-SO_2-NH-CO-N\underset{N}{\overset{}{\diagdown}}\overset{O}{\overset{\|}{C}}\diagup N-R^1 \diagdown\!\!=\!\!\diagup R^2 \quad (II)$$

in which $R^1$ and $R^2$ have the abovementioned meaning, are reacted with nucleophilic compounds of the general formula (III)

$$R^3-Q-H \quad (III)$$

in which

Q and $R^3$ have the abovementioned meaning, where appropriate in the presence of an acid acceptor and where appropriate in the presence of a diluent, or if (b) triazolinones of the general formula (IV)

$$H-N\underset{N}{\overset{}{\diagdown}}\overset{O}{\overset{\|}{C}}\diagup N-R^1 \diagdown\!\!=\!\!\diagup R^2 \quad (IV)$$

in which $R^1$ and $R^2$ have the abovementioned meaning, are reacted with chlorosulphonyl isocyanate, where appropriate in the presence of a diluent, and the resulting chlorosulphonylarinocarbonyltriazolinones of the formula (II)—above—are reacted, without intermediate isolation, with nucleophilic compounds of the general formula (III)—above—, where appropriate in the presence of an acid acceptor and where appropriate in the presence of a diluent, and, where appropriate, the compounds of the formula (I) which are obtained by processes (a) or (b) are converted into salts using customary methods.

Further possible methods for preparing the novel compounds of the formula (I) are listed below, with Q, $R^1$, $R^2$ and $R^3$ in each case having the abovementioned meaning:

(c) reaction of isocyanates of the formula (V) with triazolinones of the formula (IV):

$$R^3-Q-SO_2-N=C=O + H-N\underset{\underset{(IV)}{N}}{\overset{}{\diagdown}}\overset{O}{\overset{\|}{C}}\diagup N-R^1 \diagdown\!\!=\!\!\diagup R^2 \longrightarrow$$
(V)

$$R^3-Q-SO_2-NH-CO-N\underset{\underset{(I)}{N}}{\overset{}{\diagdown}}\overset{O}{\overset{\|}{C}}\diagup N-R^1 \diagdown\!\!=\!\!\diagup R^2$$

(d) reaction of aminosulphonyl compounds of the formula (VI) with oxycarbonyltriazolinones of the formula (VII) (R: alkyl, aralkyl or aryl):

$$R^3-Q-SO_2-NH_2 + R-O-CO-N\underset{\underset{(VII)}{N}}{\overset{}{\diagdown}}\overset{O}{\overset{\|}{C}}\diagup N-R^1 \diagdown\!\!=\!\!\diagup R^2 \xrightarrow{-ROH}$$
(VI)

-continued

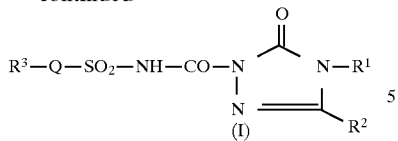

(e) reaction of sulphonylurethanes of the formula (VIII) with triazolinones of the formula (IV) (R: alkyl, aralkyl or aryl):

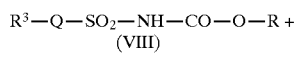

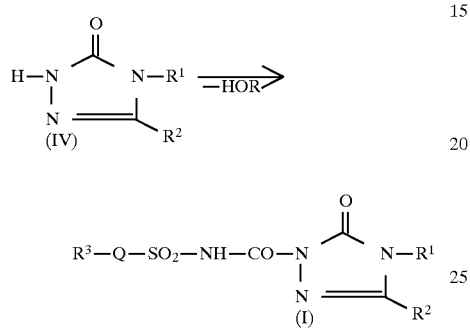

The novel sulphonylaminocarbonyltriazolinones of the general formula (I) are notable for their powerful herbicidal activity.

Surprisingly, the novel compounds of the formula (I) exhibit a substantially more powerful herbicidal effect than structurally similar, known 4,5-dimethyl-2-(2-chlorophenylsulphonyl-aminocarbonyl)-2, 4dihydro-3H-1, 2,4-triazol-3-one.

The invention preferably relates to compounds of the formula (I), in which

Q represents oxygen, sulphur or the grouping —N(R$^4$)—,

R$^1$ represents hydrogen, hydroxyl or amino, represents $C_2$–$C_{10}$-alkylidenamino, represents $C_1$–$C_6$-alkyl which is optionally substituted by fluorine, chlorine, bromine, cyano, $C_1$–$C_4$-alkoxy, $C_1$–$C_4$-alkylcarbonyl or $C_1$–$C_4$-alkoxy-carbonyl, represents $C_3$–$C_6$-alkenyl or $C_3$–$C_6$-alkinyl which are in each case optionally substituted by fluorine, chlorine and/or bromine, represents $C_3$–$C_6$-cycloalkyl which is optionally substituted by fluorine, chlorine, bromine and/or $C_1$–$C_4$-alkyl, represents phenyl-$C_1$–$C_3$-ally which is optionally substituted by fluorine, chlorine, bromine, cyano, nitro, $C_1$–$C_4$-alkyl, trifluoromethyl, $C_1$_$C_4$-alkoxy and/or $C_1$–$C_4$-alkoxycarbonyl, represents phenyl which is optionally substituted by fluorine, chlorine, bromine, cyano, nitro, $C_1$_$C_4$-alkyl, trifluoromethyl, $C_f$–$C_4$-alkoxy, fluorine- and/or chlorine-substituted $C_1$_$C_3$-alkoxy, $C_1$–$C_4$-alkylthio, fluorine- and/or chlorine-substituted $C_1$–$C_3$-alkylthio, $C_1$–$C_4$-alkylsulphinyl, $C_1$–$C_4$-alkylsulphonyl and/or $C_1$–$C_4$-alkoxy-carbonyl, represents $C_1$–$C_6$-alkoxy which is optionally substituted by fluorine, chlorine, cyano, phenyl, $C_1$–$C_4$-alkoxy or $C_1$–$C_4$-alkoxy-carbonyl, represents $C_3$–$C_6$-alkenyloxy, represents $C_1$–$C_4$ -alkylamino, $C_3$–$C_6$-cycloalkylamino or di-($C_1$–$C_4$-alky)-amino which are optionally substituted by fluorine, cyano, $C_1$–$C_4$-alkoxy or $C_1$–$C_4$-alkoxy-carbonyl, or represents $C_1$–$C_6$-alkanoylamino, R$^1$ represents hydrogen, hydroxyl, mercapto, amino or halogen, represents $C_1$–$C_6$-alkyl or $C_2$–$C_6$-alkenyl which are optionally substituted by fluorine, chlorine, bromine, cyano, $C_3$–$C_6$-cycloalkyl, $C_1$–$C_4$-alkoxy, $C_1$–$C_4$-alkylthio or $C_1$–$C_4$ -alkoxy-carbonyl, represents $C_3$–$C_6$-cycloalkyl which is optionally substituted by fluorine, chlorine, bromine and/or $C_1$–$C_4$-alkyl, represents cyclohexenyl, represents phenyl-$C_1$–$C_3$-alkyl which is optionally substituted by fluorine, chlorine, bromine, cyano, nitro, $C_1$_$C_4$-alkyl, trifluoromethyl, $C_1$–$C_4$-alkoxy and/or $C_1$–$C_4$-alkoxy-carbonyl, represents phenyl which is optionally substituted by fluorine, chlorine, bromine, cyano, nitro, $C_1$_$C_4$-alkyl, trifluoromethyl, $C_1$–$C_4$-alkoxy, fluorine- and/or chlorine-substituted $C_1$–$C_3$-alkoxy, $C_1$–$C_4$-alkylthio, fluorine- and/or chlorine-substituted $C_1$_$C_3$-alkylthio, $C_1$–$C_4$-alkyl-sulphinyl, $C_1$–$C_4$-alkylsulphonyl and/or $C_1$–$C_4$-alkoxy-carbonyl, represents $C_1$–$C_6$-alkoxy which is optionally substituted by fluorine, chlorine, cyano, $C_3$–$C_6$-cycloalkyl, $C_1$–$C_4$-alkoxy or $C_1$–$C_4$-alkoxy-carbonyl, represents $C_3$–$C_6$-alkenyloxy, $C_3$–$C_6$-alkenyloxy or $C_3$–$C_6$-cycloalkyloxy, represents phenoxy or benzyloxy which are in each case optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, represents $C_1$–$C_6$-alkylthio, $C_1$–$C_6$-alkylsulphinyl, $C_1$–$C_6$-alkylsulphonyl, $C_3$–$C_6$-alkenylthio, $C_3$–$C_6$-alkenylthio or $C_3$–$C_6$-cycloalkylthio which are in each case optionally substituted by fluorine, chlorine, cyano, $C_1$–$C_4$-alkoxy or $C_1$–$C_4$-alkoxy-carbonyl, represents phenylthio or benzylthio which are in each case optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, represents $C_1$–$C_6$-alkylamino or $C_3$–$C_6$-alkenylamino, represents phenylamino or benzylamino which are in, each case optionally substituted by fluorine, chlorine, bromine, cyano, nitro, $C_1$–$C_4$-alkyl, trifluoromethyl, $C_1$–$C_4$-alkoxy, difluoromethoxy or trifluoromethoxy, represents di-($C_1$–$C_4$-alkyl)-amino, or represents aziridino, pyrrolidino or morpholino which are in each case optionally substituted by $C_1$–$C_4$-alkyl, R$^3$ represents phenyl, naphthyl, phenyl-$C_1$–$C_4$-alkyl or naphthyl-$C_1$–$C_4$-alkyl which are in each case substituted at least twice (identically or differently) by halogen, formyl, cyano, carboxyl or nitro, by $C_1$–$C_4$-alkyl, $C_1$–$C_4$-alkoxy, $C_1$–$C_4$-alkylthio, $C_1$–$C_4$-alkylsulphinyl or $C_1$–$C_4$-alkylsulphonyl (which are in each case optionally substituted by halogen, cyano, $C_1$–$C_4$-alkoxy or $C_1$–$C_4$-alkoxycarbonyl), by $C_1$–$C_4$-alkylsulphonyl, $C_1$–$C_4$-alkylaminosulphonyloxy, di-($C_1$–$C_4$-alkyl)-amino-sulphonyloxy, $C_1$–$C_4$-halogenoalkylsulphonyloxy, di-($C_1$$C_4$-alkyl)-aminocarbonyl or $C_1$–$C_4$-alkynylaminocarbonyl, by $C_3$–$C_6$-cycloalkyl or $C_3$–$C_6$-cycloalkyl-$C_1$–$C_4$-alkyl (which are in each case optionally substituted by halogen or $C_1$–$C_4$-alkyl), by phenyl, phenoxy, phenylthio, phenylsulphinyl, phenylsulphonyl, phenylsulphonyloxy, phenylamino, phenylcarbonyl or phenyl-$C_1$–$C_4$-alkyl (which are in each case optionally substituted by halogen, cyano, nitro, $C_1$–$C_4$-alkyl, $C_1$–$C_4$-halogenoalkoxy, $C_1$–$C_4$-alkoxy, $C$–$C_4$-halogenoalkoxy, $C_1$–$C_4$-alkylthio, $C_1$–$C_4$-halogenoalkylthio, $C_1$–$C_4$-alkoxy-carbonyl or $C_1$–$C_4$-alkoxy-amino), or by $C_1$–$C_4$-alkyl-carbonyl, $C_3$–$C_6$-cycloalkylcarbonyl or $C_1$–$C_4$-alkoxycarbonyl (which are in each case optionally substituted by halogen, $C_3$–$C_6$cycloalkyl or $C_1$–$C_4$-alkoxy), where one of the substituents is different from allyl, $R^4$ represents hydrogen, hydroxyl, amino or cyano, represents $C_1$–$C_6$-alkyl, $C_3$–$C_6$-alkenyl or $C_3$–$C_6$-alkinyl which are in each case optionally substituted by halogen, cyano, carboxyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylamino, di-($C_1$–$C_4$-alkyl-amino or $C_1$–$C_4$-alkoxy-carbonyl, represents $C_1$–$C_4$-alkoxy-carbonyl, represents $C_1$–$C_6$-alkoxy, $C_3$–$C_6$-alkenyloxy, benzyloxy, phenoxy or di-($C_1$–$C_4$-alkoxy) (thio)phosphoryl, or represents the following grouping $Q^1$—$R^5$, in which $Q^1$ represents —CO— or —SO$_2$—, and $R^5$ represents $C_1$–$C_6$-alkyl which is optionally substituted by halogen or $C_1$–$C_4$-alkoxy, represents $C_3$–$C_6$-cycloalkyl which is optionally substituted by halogen or $C_1$–$C_4$-alkyl, or represents phenyl which is optionally substituted by halogen, $C_1$–$C_4$-alkyl, $C_1$–$C_4$-halogenoalkyl or $C_1$–$C_4$-alkoxy.

The invention additionally relates, preferably, to sodium, potassium magnesium, calcium, ammonium, $C_1$–$C_4$-allyl-ammonium, di($C_1$–$C_4$-alkyl)-ammonium, tri-($C_1$–$C_4$-alkyl)-ammonium, $C_5$- or $C_6$-cycloalkyl-ammonium and di-($C_1$–$C_2$-alkyl)-benzyl-ammonium salts of compounds of the formula (I) in which Q, $R^1$, $R^2$ and $R^3$ have the meanings which have been given above as being preferred.

The invention relates, in particular, to compounds of the formula (I), in which

Q represents oxygen or the grouping

$R^1$ represents methyl, ethyl, n- or i-propyl, n-, i-, s- or t-butyl, dichloromethyl, fluoroethyl, chloroethyl, difluoroethyl, dichloroethyl, trifluoroethyl, trichloroethyl, chlorodifluoroethyl, tetrafluoroethyl, cyanomethyl, cyanoethyl, methoxymethyl, ethoxymethyl, methoxyethyl or ethoxyethyl, represents allyl chloroallyl, dichloroallyl or propargyl, represents cyclopropyl, benzyl or phenyl, represents methoxy, ethoxy, or n- or i-propoxy, represents allyloxy, or n- or i- or s-butoxy, represents methylamino, ethylamino, or n- or i-propylamino, or represents cyclopropylamino, dimethylamino, diethylamino or acetylamino, $R^2$ represents chlorine, bromine, methyl, ethyl, n- or i-propyl, n-, i-, s- or t-butyl, difluoromethyl, trifluoromethyl, dichloromethyl, trichloromethyl, cyanomethyl, cyanoethyl, cyclopropylmethyl, methoxymethyl, ethoxymethyl, methoxyethyl, ethoxyethyl, methylthiomethyl, ethylthiomethyl, methylthioethyl or ethylthioethyl, represents cyclopropyl, difluorocyclopropyl or dichlorocyclopropyl, represents phenyl or benzyl, represents methoxy, ethoxy, or n- or i-propoxy, represents difluoromethoxy, trifluoromethoxy, fluoroethoxy, difluoroethoxy or trifluoroethoxy, represents cyclopropylmethoxy, represents methoxymethoxy, ethoxymethoxy, methoxyethoxy or ethoxyethoxy, represents phenoxy or benzyloxy, represents methylthio, ethylthio, or n- or i-propylthio, represents fluoroethylthio, difluoroethylthio or trifluoroethylthio, allylthio, propargylthio, cyclopropylmethylthio, methylsulphinyl, ethylsulphinyl, methylsulphonyl, ethylsulphonyl, phenylthio or benzylthio, represents methylamino ethylamino, n- or i-propylamino, phenylamino or benzylamino, represents dimethylamino, diethylamino, dipropylamino, methylethylamino or methylpropylamino, represents aziridino or represents pyrrolidino, piperidino or morpholino which are in each case optionally substituted by methyl or ethyl, $R^3$ represents phenyl, phenylmethyl or phenylethyl which are substituted in the 2 position and in the 6 position (identically or differently) by fluorine, chlorine, bromine, formyl, cyano, carboxyl or nitro, by methyl, ethyl, n- or i-propyl, methoxy, ethoxy, methylthio, ethylthio, methylsulphinyl, ethylsulphinyl, methylsulphonyl or ethylsulphonyl (which are in each case optionally substituted by fluorine, chlorine, cyano, methoxy, ethoxy, methoxycarbonyl or ethoxycarbonyl), by methylsulphonyloxy, ethylsulphonyloxy, methylamino-sulphonyloxy, ethylaminosulphonyloxy, dimethylamino-sulphonyloxy, diethylaminosulphonyloxy, trifluoromethylsulphonyloxy, dimethylaminocarbonyl or diethylaminocarbonyl, by cyclohexyl or cyclohexylmethyl (which are in each case optionally substituted by chlorine, methyl or ethyl), by phenyl, phenoxy, phenylthio, phenylsulphonyl, phenylsulphonyloxy, phenylamino, phenylcarbonyl, phenylmethyl or phenylethyl (which are in each case optionally substituted by fluorine, chlorine, cyano, nitro, methyl, ethyl, trifluoromethyl, methoxy, ethoxy, difluoromethoxy, trifluoromethoxy, methylthio, ethylthio, trifluoromethylthio, methoxycarbonyl or ethoxycarbonyl), or by acetyl, propionyl, n- or i-butyroyl, cyclopropylcarbonyl, methoxycarbonyl or ethoxycarbonyl (which are in each case optionally substituted by fluorine, chlorine, cyclopentyl, cyclohexyl, methoxy or ethoxy), where one of the substituents is different from alkyl, $R^4$ represents hydrogen, cyano, cyanomethyl, cyanoethyl, difluoromethyl, methoxymethyl, ethoxymethyl, methoxyethyl, ethoxyethyl, methoxycarbonylmethyl, ethoxycarbonylmethyl, methoxy-carbonylethyl, ethoxycarbonylethyl, allyl, propargyl, methoxycarbonyl, ethoxycarbonyl, methoxy, ethoxy, allyloxy or benzyloxy, or represents the grouping $Q^1$—$R^5$, in which $Q^1$ represents —CO— or —SO$_2$—, and $R^5$ represents methyl, ethyl or propyl which are in each case optionally substituted by fluorine, chlorine, methoxy or ethoxy, represents cyclopropyl, cyclobutyl, cyclopentyl or cyclohexyl which are in each case optionally substituted by fluorine, chlorine, methyl or ethyl, or represents phenyl which is optionally substituted by fluorine, chlorine, bromine, methyl, ethyl, trifluoromethyl, methoxy or ethoxy.

The above listed general radical definitions, or those listed in preference ranges, apply both to the end products of the formula (I) and also, in a corresponding manner, to the starting compounds and/or intermediates which are in each case required for the preparation. These radical definitions ray be combined arbitrarily among themselves, that is between the given preferred ranges as well.

The hydrocarbon radicals which are mentioned in the radical definitions, such as alkyl, alkenyl or alkinyl, also in combinations with heteroatoms, such as in alkoxy, alkylthio or alkylamino, are straight-chain or branched, even when this is not expressly indicated.

In general, halogen represents fluorine, chlorine, bromine or iodine, preferably fluorine, chlorine or bromine, in particular fluorine or chlorine.

If, for example, 2-chlorosulphonylaminocarbonyl-4-ethoxyl-5-ethyl-2,4dihydro3H-1,2,4-triazol-3-one and 2-amino-3-fluoro-acetophenone are used as the starting compounds, the course of the reaction in the novel process (a) can then be outlined by the following formula scheme:

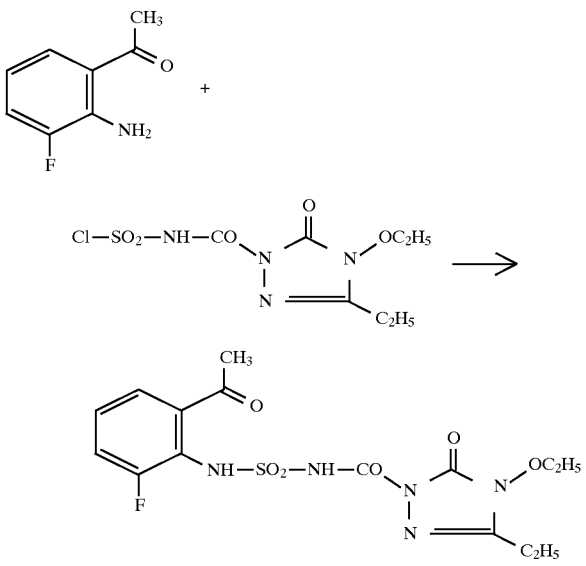

If, for example, 4-ethyl-5-ethylthio-2,4-dihydro-3H-1,2,4-triazol-3-one and chlorosulphonyl isocyanate, and subsequently methyl 2-amino-6-fluoro-benzoate, are used as starting compounds, the course of the reaction in the novel process (b) can then be outlined by the following formula scheme:

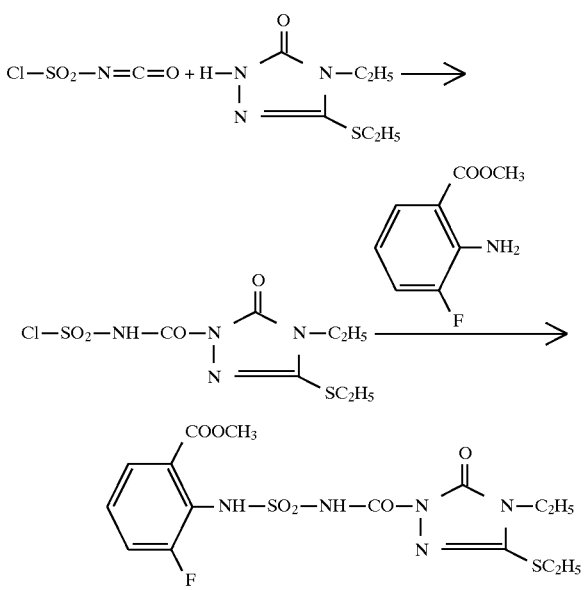

The chlorosulphonylaminocarbonyltriazolinones which are to be used as starting compounds in the novel process (a) for preparing compounds of the formula (I) are defined generally by the formula (II).

In formula (II), $R^1$ and $R^2$ preferably or in particular have those meanings which have already been indicated above, in connection with the description of the novel compounds of the formula (I), as being especially or in particular preferred for $R^1$ and $R^2$.

The following may be mentioned as examples of the starting compounds of the formula (II):
4,5-dimethyl-, 4,5-diethyl-, 4-ethyl-5-methyl-, 5-ethyl-4-methyl-, 4-methyl-5-propyl-,4-ethyl-5-propyl-, 4-cyclopropyl-5-ethyl-, 5-cyclopropyl-4-methyl-, 5-cyclopropyl4- ethyl-,4-methyl-5-chloro-, 4-ethyl-5-chloro-, 4-methyl-5-bromo-, 4ethyl-5-bromo-,4-cyclopropyl-5-chloro-, 4-cyclopropyl-5-bromo-, 4-methoxy-5-methyl-, 4-ethoxy-5-methyl-,4-ethoxy-5-ethyl-, 4-methoxy-5-ethyl-, 4-methyl-5-methoxy-, ethyl-5-methoxy-,4-methyl-5-ethoxy-, 4-ethyl-5-ethoxy-, 4-methyl-5-methylthio-, 4-methyl-5-ethylthio-, 4-ethyl-5-methylthio-, 4-ethyl-5-ethylthio-, 4-cyclopropyl-5-methoxy-,4-cyclopropyl-5-ethoxy-, 4-cyclopropyl-5-methylthio-, 4-cyclopropyl-5-ethylthio-,4-methoxy-5-cyclopropyl-, 4-ethoxy-5-cyclopropyl-, 4-methoxy-5-ethoxy-, 4,5-dimethoxy-,4,5-diethoxy-, 4-methyl-5-dimethylamino-, 4-ethyl-5-dimethylamino- and 4-cyclopropyl-5-dimethylamino-2-chlorosulphonylaminocarbonyl-2,4-dihydro-3H-1,2,4,-triazol-3-one.

The chlorosulphonylaminocarbonyltriazolinones of the general formula (II) have still not been disclosed in the literature; they are the subject-matter, as novel compounds, of a previous application (cf DE-P 4234801/LeA 29398 of 15.10.1992).

The compounds of the formula (II) are obtained if triazolinones of the general formula (IV)

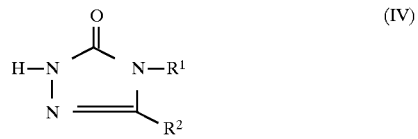

in which
$R^1$ and $R^2$ have the abovementioned meaning,
are reacted with chlorosulphonyl isocyanate, where appropriate in the presence of a diluent, such as methylene chloride, at temperatures of between −20° C. and +50° C., and worked up in a customary manner (cf. the preparation examples).

The nucleophilic compounds which are to be used as starting compounds in the novel processes (a) and (b) for preparing compounds of the formula (I) are defined generally by the formula (III).

In formula (III), Q and $R^3$ preferably or in particular have those meanings which have already been indicated above, in connection with the description of the novel compounds of the formula (I), as being especially or in particular preferred for Q and $R^3$.

The starting compounds of the formula (III) are known organic synthesis chemicals.

The triazolinones which are to be used as starting compounds in the novel processes (a) and (b) for preparing compounds of the formula (I) are defined generally by the formula (IV).

In formula (IV), $R^1$ and $R^2$ preferably or in particular have those meanings which have already been indicated above, in connection with the description of the novel compounds of the formula (I), as being especially or in particular preferred for $R^1$ and $R^2$.

The starting compounds of formula (IV) are known and/or can be prepared by processes which are known per se (cf. EP-A 283876, EP-A 294666, EP-A 301946, EP-A 298371, EP-A 341489, EP-A 399294, EP-A 398096, EP-A 422469, EP-A 425948, EP-A 431291, EP-A 477646, DE-A 4110795).

The novel processes (a) and (b) for preparing the novel compounds of the formula (I) are preferably carried out using diluents. In this context, virtually all inert organic solvents are suitable for use as diluents. These solvents preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as acetonitrile and proprionitrile, amides, such as dimethylformamide, dimethylacetamide and N-methylpyrrolidone, and also dimethylsulphoxide, tetramethylenesulphone and hexamethylphosphoric triamide.

In the novel processes (a) and (b), all the acid-binding agents which are customarily usable for reactions of this nature may be employed as acid acceptors. Those which are preferred are alkali metal hydroxides, such as sodium and potassium hydroxide, alkaline earth metal hydroxides, such as calcium hydroxide, alkali metal carbonates and alkali metal alcoholates, such as sodium and potassium carbonate, and sodium and potassium tert-butoxide, and, in addition, basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbeneylamine, N,N-dimethyl-aniline, pyridine, 2-methyl-, 3-methyl-, 4methyl-,2,4-dimethyl-, 2,6-dimethyl-, 2-ethyl-, 4-ethyl- and 5-ethyl-2-methyl-pyridine, 1,5-diazabicyclo [4.3.0]-non-5-ene (DBN), 1,8-diazabicyclo-[5.4.0]-undec-7-ene (DBU) and 1,4-diazabicyclo-[2.2.2]-octane (DABCO).

In the novel processes (a) and (b), the reaction tee s may be varied over a relatively wide range. In general, the processes are carried out at temperatures of between –20° C. and +80° C., preferably at temperatures of between –10° C. and +50° C.

In general, the novel processes (a) and (b) are carried out under standard pressure. However, it is also possible to carry them out under elevated or reduced pressure.

In order to carry out the novel processes (a) and (b), the starting compounds which are required in each case are in general employed in approximately equimolar quantities. However, it is also possible to use one of the components which is employed in each case in a relatively large excess. In general, the reactions are carried out in a suitable diluent in the presence of an acid acceptor, and the reaction mixture is stirred for several hours at the temperature required in each case. In the novel processes (a) and (b), the working-up is in each case effected using customary methods (cf the preparation examples).

Where appropriate, salts may be prepared from the novel compounds of the general formula (I). These salts are obtained, in a simple manner, using customary methods for salt formation, for example by dissolving or dispersing a compound of the formula (I) in a suitable solvent such as methylene chloride, acetone, tert-butyl methyl ether or toluene, and adding a suitable base. The salts can then be isolated—where appropriate after a relatively long period of stirring—by concentrating or by filtering with suction.

The active compounds according to the invention can be used as defoliants, desiccants, haulm destroyers and, especially, as weedkillers. By weeds, in the broadest sense, there are to be understood all plants which grow in locations where they are undesired. Whether the substances according to the invention act as total or selective herbicides depends essentially on the amount used.

The novel active compounds can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, fruit orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The novel compounds of the formula (I) are particularly suitable for selectively controlling monocotyledonous and dicotyledonous weeds in monocotyledonous cultures both in the pre-emergence and in the post-emergence processes.

In addition to this, the novel active compounds (I) also exhibit interesting side effects, namely a foliar insecticidal effect and fungicidal effects, in particular against Pyricularia oryzae and against Erysiphe graminis.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are suitable are mainly: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffis, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground aural minerals such as kaolins, clays, talc, chalk quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolyzates; suitable dispersants are: for example lignin-sulphite waste liquors and methylcellulose.

Adhesives such as carboxymethylcellulose and natural and synthetic polymers in the form of powders, granules or latexes such as gum polyvinyl acetate, or else nd polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr, aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metchlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethaben imazayr and imazaquin; nitriles such as, for example, bromoxynil, dichlobenil and ioxynil; oxyacetamides such as, for example, mefenacet; sulphonylureas such as, for example, amidosulfron, bensulfuron-methyl, chlorimuron-ethyl, chlorsulfuron, cinosulfuron, metsulfuron-methyl, nicosulfuron, primisulfuron, pyrazosuliron-ethyl, thifensulfron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difeenzoquat, dithiopyr, ethofumesate, fluorochloridone, glufo-sinate, glyphosate, isoxaben, pyridate, quinchlorac, quinmerac, sulphosate and tridiphane.

Mixtures with other known active compounds such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 2 kg per ha.

The preparation and use of the novel active compounds can be seen from the examples which follow.

PREPARATION EXAMPLES

Example 1

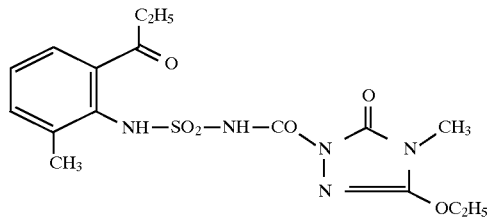

(Process (a))

2.85 g (0.01 mol) of 2-chlorosulphonylaminocarbonyl-4-methyl-5-ethoxy-2,4-dihydro-3H-1,2,4-triazol-3-one are initially introduced into 150 ml of methylene chloride, and 3.26 g (0.02 mol) of 2-amino-3-methyl-propiophenone are added to this mixture at 20° C. The reaction mixture is stirred at 20° C. for 2 hours. It is then washed three times with 50 ml of water on each occasion, dried with sodium sulphate and filtered. The filtrate is concentrated under a water pump vacuum, and the residue is recrystallized from ethanol.

3.58 g (87% of theory) of 2-(2-methyl-6-propionyl-phenylamino-sulphonylaminocarbonyl)-4-methyl-5-ethoxy-2,4-dihydro-3H-1,2,4-triazol-3-one are obtained with a melting point of 134° C.

The compounds of the formula (I) which are listed in Table 1 below may, for example, be prepared in analogy with Example 1 and in accordance with the general description of the novel preparation processes.

TABLE 1

$$R^3-Q-SO_2-NH-CO-N\underset{\underset{R^2}{\overset{\|}{N}}}{\overset{O}{\|}}N-R^1 \quad (I)$$

Preparation examples for the compounds of the formula (I) (in Table 1, "D" stands for "decomposition on melting")

| Ex. No. | Q  | $R^1$  | $R^2$       | $R^3$              | Physical Data |
|---------|----|--------|-------------|--------------------|---------------|
| 2       | NH | $CH_3$ | $CH_3$      | 2-CHO-5-Cl-phenyl  |               |
| 3       | NH | $CH_3$ | $N(CH_3)_3$ | 2-CHO-5-Cl-phenyl  |               |
| 4       | NH | $CH_3$ | $OC_2H_5$   | 2-CHO-5-Cl-phenyl  |               |
| 5       | NH | $CH_3$ | $OC_2H_5$   | 2-CHO-5-F-phenyl   |               |
| 6       | NH | $C_2H_5$ | $CH_3$    | 2-CHO-5-$CH_3$-phenyl |            |
| 7       | NH | $OCH_3$ | $nC_3H_7$  | 2-CHO-5-$CH_3$-phenyl |            |
| 8       | NH | $CH_3$ | cyclopropyl | 2-CHO-5-$CH_3$-phenyl |            |

TABLE 1-continued $$R^3-Q-SO_2-NH-CO-N\underset{N}{\overset{\underset{\displaystyle\|}{O}}{\underset{\|}{C}}}\underset{R^2}{\overset{N-R^1}{=\!\!=}} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 9 | NH | CH₃ | SCH₃ | 2-CHO-6-CH₃-phenyl | |
| 10 | NH | CH₃ | N(CH₃)₂ | 2-COCH₃-5-F-phenyl | |
| 11 | NH | C₂H₅ | OC₂H₅ | 2-COCH₃-5-Cl-phenyl | |
| 12 | NH | CH₃ | Cl | 2-COCH₃-5-Cl-phenyl | |
| 13 | NH | OCH₃ | CH₃ | 2-COCH₃-5-Cl-phenyl | |
| 14 | NH | CH₃ | OC₂H₅ | 2-COC₂H₅-5-F-phenyl | |
| 15 | NCH₃ | CH₃ | OC₂H₅ | 2-COC₂H₅-5-F-phenyl | |

TABLE 1-continued
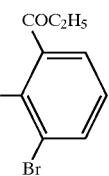
(I)
Preparation examples for the compounds of the formula (I) (in Table 1, "D" stands for "decomposition on melting")
| Ex. No. | Q | R¹ | R² | R³ | Physical Data |
|---|---|---|---|---|---|
| 16 | NH | OCH₃ | CH₃ | 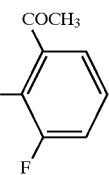 COC₂H₅ / Br | |
| 17 | O | CH₃ | OCH₃ | 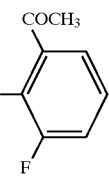 COCH₃ / F | |
| 18 | NH | CH₃ | SC₂H₅ |  COCH₃ / F | |
| 19 | NH | CH₃ | △ | 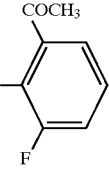 COCH₃ / F | |
| 20 | S | C₂H₅ | OCH₃ | 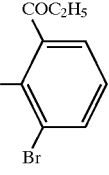 COC₂H₅ / Br | |
| 21 | NH | CH₃ | N(CH₃)₂ | 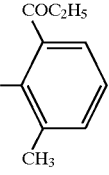 COC₂H₅ / CH₃ | M.p.: 117° C.(D) |
| 22 | NC₂H₅ | CH₃ | CH₃ | 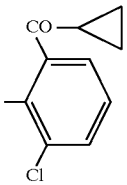 CO-△ / Cl | |

TABLE 1-continued $$R^3-Q-SO_2-NH-CO-N \overset{\underset{N}{|}}{\underset{\parallel}{\phantom{|}}} \overset{O}{\underset{\phantom{|}}{\overset{\parallel}{C}}} N-R^1 \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 23 | NH | CH₃ | OC₂H₅ | 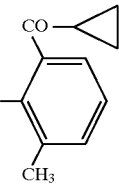 | M.p.: 154° C.(D) |
| 24 | NH | CH₃ | OCH₃ | 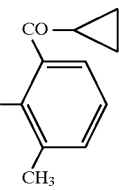 | M.p.: 138° C. |
| 25 | NH | CH₃ | OC₂H₅ | 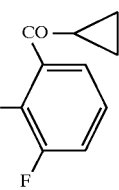 | M.p.: 145° C.(D) |
| 26 | NH | CH₃ | SC₂H₅ | 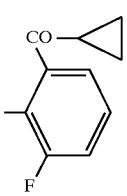 | M.p.: 107° C. |
| 27 | NCH₃ | OCH₃ | C₂H₅ | 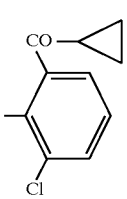 | |
| 28 | O | CH₃ | OC₂H₅ | 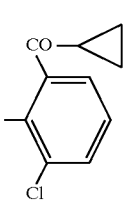 | |
| 29 | NH | CH₃ | OC₂H₅ | 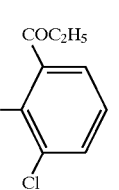 | M.p.: 129° C.(D) |

TABLE 1-continued $$R^3-Q-SO_2-NH-CO-N\underset{N}{\overset{\overset{O}{\underset{\|}{C}}-N-R^1}{\diagdown}}\underset{R^2}{\diagup} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 30 | NH | cyclopropyl | CH₃ | 2-COOC₂H₅-3-Cl-phenyl | |
| 31 | NH | cyclopropyl | OCH₃ | 2-(CO-cyclopropyl)-4-C₂H₅-phenyl | |
| 32 | NH | cyclopropyl | OC₂H₅ | 2-COCH₃-4-CH₃-phenyl | |
| 33 | NH | CH₃ | OCH₃ | 2-COOC₂H₅-4-C₂H₅-phenyl | M.p.: 147° C. |
| 34 | NH | CH₃ | OCH₃ | 2-COCH₃-4-CH₃-phenyl | |
| 35 | NH | CH₃ | CH₃ | 2-(CO-cyclopropyl)-4-Br-phenyl | |
| 36 | NH | CH₃ | SCH₃ | 2-COOC₂H₅-4-C₂H₅-phenyl | M.p.: 142° C. |

TABLE 1-continued $$R^3-Q-SO_2-NH-CO-N\underset{N}{\overset{\overset{\displaystyle O}{\|}}{\underset{\|}{C}}}\underset{R^2}{\overset{N-R^1}{=}} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 37 | NH | CH₃ | SCH₃ | 2-COC₂H₅, 6-OCH₃-phenyl | |
| 38 | O | CH₃ | OCH₃ | 2-COC₂H₅, 6-OCH₃-phenyl | |
| 39 | O | CH₃ | OC₂H₅ | 2-COC₂H₅, 6-SCH₃-phenyl | |
| 40 | NH | CH₃ | OC₂H₅ | 2-COC₂H₅, 5-F-phenyl | M.p.: 136° C.(D) |
| 41 | NH | OCH₃ | OC₂H₅ | 2-COC₂H₅, 5-F-phenyl | |
| 42 | NH | cyclopropyl | OCH₃ | 2-COC₂H₅, 5-F-phenyl | |
| 43 | NH | CH₃ | SCH₃ | 2-COCH₃, 5-C₂H₅-phenyl | |

TABLE 1-continued $$R^3-Q-SO_2-NH-CO-N\underset{N}{\overset{\overset{\displaystyle O}{\|}}{\underset{|}{C}}}\underset{R^2}{N-R^1} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 44 | NH | CH₃ | OC₂H₅ | 2-COCH₃, 5-C₂H₅-phenyl | |
| 45 | NH | OC₂H₅ | CH₃ | 2-COCH₃, 5-C₂H₅-phenyl | |
| 46 | O | CH₃ | OC₂H₅ | 2-COCH₃, 5-Br-phenyl | |
| 47 | NCH₃ | CH₃ | OC₂H₅ | 2-COCH₃, 5-Br-phenyl | |
| 48 | NH | CH₃ | OC₂H₅ | 2-CHO, 5-Br-phenyl | |
| 49 | NH | CH₃ | OC₂H₅ | 2-CHO, 5-C₂H₅-phenyl | |
| 50 | NH | CH₃ | OCH₃ | 2-CHO, 5-C₂H₅-phenyl | |

TABLE 1-continued $$R^3-Q-SO_2-NH-CO-N(-N=CR^2)(C(=O)-N(R^1))  \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 51 | S | OCH₃ | OC₂H₅ | 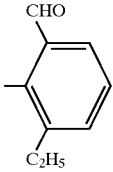 2-CHO, 3-C₂H₅-phenyl | |
| 52 | NH | OCH₃ | OCH₃ | 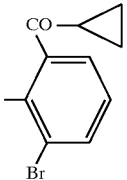 2-(cyclopropyl-CO), 4-Br-phenyl | |
| 53 | NH | CH₃ | OC₂H₅ | 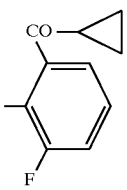 2-(cyclopropyl-CO), 4-F-phenyl | |
| 54 | NH | cyclopropyl | CH₃ |  2-(cyclopropyl-CO), 4-F-phenyl | |
| 55 | NCH₃ | CH₃ | OC₂H₅ | 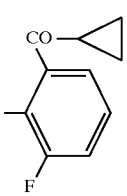 2-(cyclopropyl-CO), 4-OCH₃-phenyl | |
| 56 | NH | CH₃ | SCH₃ | 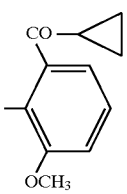 2-OCHF₂, 4-CH₃-phenyl | M.p.: 143° C. |
| 57 | NH | CH₃ | SC₂H₅ | 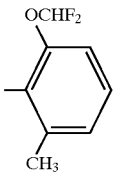 2-OCHF₂, 4-CH₃-phenyl | M.p.: 129° C. |

TABLE 1-continued $$R^3-Q-SO_2-NH-CO-N\underset{N}{\overset{O}{\underset{\|}{\big\|}}}\underset{R^2}{\overset{N-R^1}{\big|}}\quad(I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 58 | NH |  | SCH₃ | 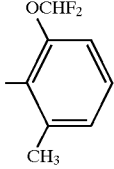 OCHF₂ / CH₃ | |
| 59 | NH |  | SC₂H₅ | 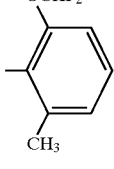 OCHF₂ / CH₃ | M.p.: 161° C. |
| 60 | NH | CH₃ | C₂H₅ | 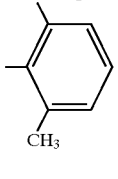 OCHF₂ / CH₃ | M.p.: 108° C. |
| 61 | NH | CH₃ | C₃H₇ | 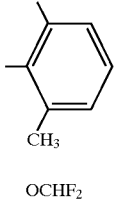 OCHF₂ / CH₃ | |
| 62 | NH | CH₃ | C₄H₉ | 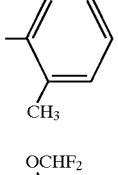 OCHF₂ / CH₃ | |
| 63 | NH | CH₃ |  | 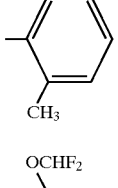 OCHF₂ / CH₃ | |
| 64 | NH |  | C₂H₅ | 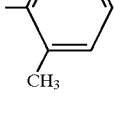 OCHF₂ / CH₃ | |

TABLE 1-continued $$R^3-Q-SO_2-NH-CO-N\underset{N}{\overset{\overset{\displaystyle O}{\|}}{\underset{\|}{\bigg\langle}}}\overset{N-R^1}{\underset{R^2}{\big\|}} \quad (I)$$

Preparation examples for the compounds of the formula (I) (in Table 1,
"D" stands for "decomposition on melting")

| Ex. No. | Q | R¹ | R² | R³ | Physical Data |
|---|---|---|---|---|---|
| 65 | NH | ▷ (cyclopropyl) | $C_3H_7$ | 2-OCHF₂-3-CH₃-phenyl | |
| 66 | NH | ▷ (cyclopropyl) | $C_4H_9$ | 2-OCHF₂-3-CH₃-phenyl | |
| 67 | NH | ▷ (cyclopropyl) | ▷ (cyclopropyl) | 2-OCHF₂-3-CH₃-phenyl | |
| 68 | NH | $OCH_3$ | $CH_3$ | 2-OCHF₂-3-CH₃-phenyl | |
| 69 | NH | $OCH_3$ | $C_2H_5$ | 2-OCHF₂-3-CH₃-phenyl | |
| 70 | NH | $OCH_3$ | $C_3H_7$ | 2-OCHF₂-3-CH₃-phenyl | |
| 71 | NH | $OCH_3$ | ▷ (cyclopropyl) | 2-OCHF₂-3-CH₃-phenyl | |

TABLE 1-continued $$R^3-Q-SO_2-NH-CO-N\underset{N}{\overset{\overset{\displaystyle O}{\|}}{\underset{\|}{C}}}\underset{R^2}{\overset{N-R^1}{=}}\quad (I)$$

Preparation examples for the compounds of the formula (I) (in Table 1, "D" stands for "decomposition on melting")

| Ex. No. | Q  | R¹        | R²     | R³                                  | Physical Data |
|---------|-----|-----------|--------|-------------------------------------|---------------|
| 72      | NH | OC₂H₅    | CH₃   | OCHF₂ / CH₃ (2-OCHF₂, 6-CH₃ phenyl) |               |
| 73      | NH | OC₂H₅    | C₂H₅  | OCHF₂ / CH₃                         |               |
| 74      | NH | OC₂H₅    | C₃H₇  | OCHF₂ / CH₃                         |               |
| 75      | NH | OC₂H₅    | cyclopropyl | OCHF₂ / CH₃                    |               |
| 76      | NH | N(CH₃)₂  | OCH₃  | OCHF₂ / CH₃                         |               |
| 77      | NH | N(CH₃)₂  | OC₂H₅ | OCHF₂ / CH₃                         |               |
| 78      | NH | N(CH₃)₂  | OC₃H₇ | OCHF₂ / CH₃                         |               |

TABLE 1-continued

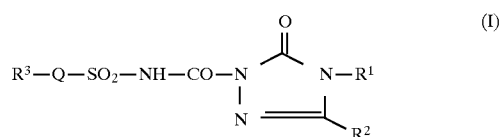

Preparation examples for the compounds of the formula (I) (in Table 1, "D" stands for "decomposition on melting")

| Ex. No. | Q | R¹ | R² | R³ | Physical Data |
|---|---|---|---|---|---|
| 79 | NH | N(CH₃)₂ | OCH₂CF₃ | 2-OCHF₂, 4-CH₃-phenyl | |
| 80 | NH | CH₃ | Cl | 2-OCHF₂, 4-CH₃-phenyl | |
| 81 | NH | CH₃ | Br | 2-OCHF₂, 4-CH₃-phenyl | M.p.: 164° C. |
| 82 | NH | CH₃ | N(CH₃)₂ | 2-OCHF₂, 4-CH₃-phenyl | |
| 83 | NH | cyclopropyl | N(CH₃)₂ | 2-OCHF₂, 4-CH₃-phenyl | |
| 84 | NH | cyclopropyl | Cl | 2-OCHF₂, 4-CH₃-phenyl | |
| 85 | NH | cyclopropyl | Br | 2-OCHF₂, 4-CH₃-phenyl | M.p.: 150° C. |

TABLE 1-continued

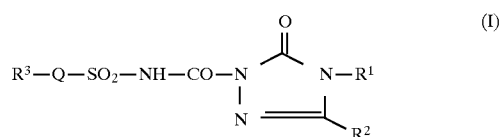

Preparation examples for the compounds of the formula (I) (in Table 1, "D" stands for "decomposition on melting")

| Ex. No. | Q | R¹ | R² | R³ | Physical Data |
|---|---|---|---|---|---|
| 86 | NH | $CH_3$ | $OCH_3$ | $OCHF_2$-phenyl-$CH_3$ | M.p.: 148° C. |
| 87 | NH | $CH_3$ | $OC_2H_5$ | $OCHF_2$-phenyl-$CH_3$ | |
| 88 | NH | $CH_3$ | $OC_3H_7$ | $OCHF_2$-phenyl-$CH_3$ | |
| 89 | NH | $CH_3$ | OCH2CF3 | $OCHF_2$-phenyl-$CH_3$ | |
| 90 | NH | $C_2H_5$ | $OCH_3$ | $OCHF_2$-phenyl-$CH_3$ | |
| 91 | NH | $C_2H_5$ | $OC_2H_5$ | $OCHF_2$-phenyl-$CH_3$ | |
| 92 | NH | $C_2H_5$ | $OC_3H_7$ | $OCHF_2$-phenyl-$CH_3$ | |

TABLE 1-continued $$R^3-Q-SO_2-NH-CO-N\underset{N}{\overset{\overset{O}{\|}}{\underset{\|}{C}}}\underset{R^2}{N-R^1} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 93 | NH | C₂H₅ | OCH₂CF₃ | OCHF₂, CH₃-phenyl | |
| 94 | NH | cyclopropyl | OCH₃ | OCHF₂, CH₃-phenyl | |
| 95 | NH | cyclopropyl | OC₂H₅ | OCHF₂, CH₃-phenyl | |
| 96 | NH | cyclopropyl | OC₃H₇ | OCHF₂, CH₃-phenyl | |
| 97 | NH | CH₃ | OCH₃ | OCF₃, CH₃-phenyl | |
| 98 | NH | CH₃ | OC₂H₅ | OCF₃, CH₃-phenyl | |
| 99 | NH | CH₃ | OC₃H₇ | OCF₃, CH₃-phenyl | |

TABLE 1-continued $$R^3-Q-SO_2-NH-CO-N\overset{\displaystyle O}{\underset{N}{\underset{\parallel}{\big|}}}\overset{\displaystyle \big\|}{\underset{R^2}{C}}N-R^1 \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 100 | NH | CH₃ | OCH₃ | 2-COOCH₃-4-CH₃-phenyl | |
| 101 | NH | CH₃ | OC₂H₅ | 2-COOCH₃-4-CH₃-phenyl | |
| 102 | NH | CH₃ | OC₃H₇ | 2-COOCH₃-4-CH₃-phenyl | |
| 103 | NH | C₂H₅ | OCH₃ | 2-COC₂H₅-4-CH₃-phenyl | M.p.: 131° C.(D) |
| 104 | NH | C₂H₅ | OCH₃ | 2-CO(cyclopropyl)-4-F-phenyl | M.p.: 137° C.(D) |
| 105 | NH | C₂H₅ | OCH₃ | 2-CO(cyclopropyl)-4-Cl-phenyl | M.p.: 129° C.(D) |
| 106 | NH | CH₃ | C₃H₇-i | 2-CO(cyclopropyl)-4-Cl-phenyl | M.p.: 134° C.(D) |

TABLE 1-continued $$R^3-Q-SO_2-NH-CO-N\underset{N}{\overset{\overset{\displaystyle O}{\|}}{\underset{|}{C}}}\underset{R^2}{\overset{N-R^1}{=}}\quad(I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 107 | NH | $CH_3$ | $C_3H_7$-i | CO-cyclopropyl, 2-methyl, 4-methyl phenyl | M.p.: 114° C.(D) |
| 108 | NH | $C_2H_5$ | $OCH_3$ | CO-cyclopropyl, 2-methyl, 4-methyl phenyl | M.p.: 127° C.(D) |
| 109 | NH | $C_2H_5$ | $OCH_3$ | $COC_2H_5$, 2-methyl, 4-F phenyl | M.p.: 142° C.(D) |
| 110 | NH | $CH_3$ | $N(CH_3)_2$ | CO-cyclopropyl, 2-methyl, 4-F phenyl | M.p.: 142° C.(D) |
| 111 | NH | $CH_3$ | $N(CH_3)_2$ | CO-cyclopropyl, 2-methyl, 4-methyl phenyl | M.p.: 117° C.(D) |
| 112 | NH | $CH_3$ | $C_3H_7$-i | $COC_2H_5$, 2-methyl, 4-methyl phenyl | M.p.: 104° C. |
| 113 | NH | $CH_3$ | $C_3H_7$-i | $COC_2H_5$, 2-methyl, 4-F phenyl | M.p.: 128° C. |

TABLE 1-continued $$R^3-Q-SO_2-NH-CO-N\underset{N}{\overset{\overset{\displaystyle O}{\|}}{-}}\underset{=}{C}\underset{R^2}{\overset{N-R^1}{|}} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 114 | NH | CH₃ |  | 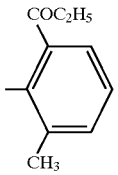 | M.p.: 141° C. |
| 115 | NH | CH₃ |  | 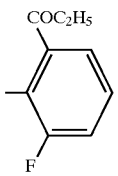 | M.p.: 158° C. |
| 116 | NH | CH₃ |  | 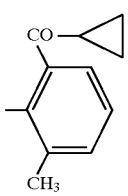 | M.p.: 101° C. |
| 117 | NH | CH₃ | SCH₃ | 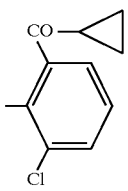 | M.p.: 161° C. |
| 118 | NH | CH₃ | SCH₃ | 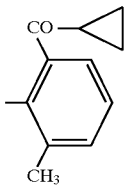 | M.p.: 166° C. |
| 119 | NH | CH₃ | SCH₃ | 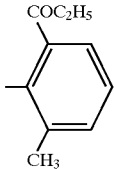 | M.p.: 151° C. |
| 120 | NH | CH₃ | SCH₃ | 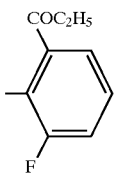 | M.p.: 146° C. |

TABLE 1-continued

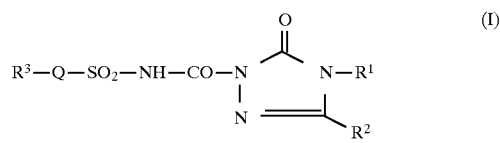

Preparation examples for the compounds of the formula (I) (in Table 1, "D" stands for "decomposition on melting")

| Ex. No. | Q | $R^1$ | $R^2$ | $R^3$ | Physical Data |
|---|---|---|---|---|---|
| 121 | NH | $CH_3$ | $OCH_3$ | 2-$COC_2H_5$, 4-F-phenyl | M.p.: 101° C. |
| 122 | NH | $CH_3$ | $OCH_3$ | 2-(CO-cyclopropyl), 4-Cl-phenyl | M.p.: 113° C. |
| 123 | NH | $CH_3$ | $OCH_3$ | 2-$COC_2H_5$, 4-$CH_3$-phenyl | M.p.: 129° C. |
| 124 | NH | $CH_3$ | $SC_2H_5$ | 2-$COC_2H_5$, 4-$CH_3$-phenyl | M.p.: 131° C. |
| 125 | NH | $CH_3$ | $SC_2H_5$ | 2-(CO-cyclopropyl), 4-Cl-phenyl | M.p.: 141° C. |
| 126 | NH | $CH_3$ | $SC_2H_5$ | 2-(CO-cyclopropyl), 4-$CH_3$-phenyl | M.p.: 145° C. |
| 127 | NH | $CH_3$ | $C_3H_7$-i | 2-(CO-cyclopropyl), 4-F-phenyl | M.p.: 112° C. |

TABLE 1-continued $$R^3-Q-SO_2-NH-CO-N\overset{\underset{N}{|}}{\underset{\parallel}{}}\overset{O}{\overset{\parallel}{C}}\underset{R^2}{N-R^1} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 128 | NH | CH₃ | SCH₃ | 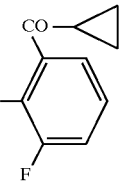 | M.p.: 139° C. |
| 129 | NH | CH₃ | 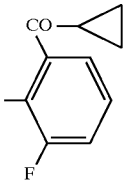 |  | M.p.: 145° C. |
| 130 | NH | CH₃ | OCH₃ | 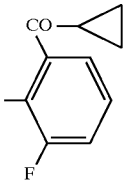 | M.p.: 161° C. |
| 131 | NH | CH₃ | OC₃H₇-i | 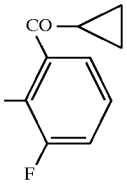 | M.p.: 135° C. |
| 132 | NH | CH₃ | OC₃H₇-i | 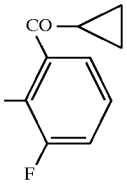 | M.p.: 164° C. |
| 133 | NH | CH₃ | OC₃H₇-i | 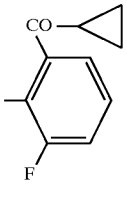 | M.p.: 138° C. |
| 134 | NH | CH₃ | OC₃H₇-i | 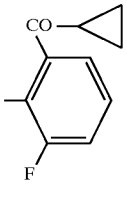 | M.p.: 156° C. |

TABLE 1-continued $$R^3-Q-SO_2-NH-CO-N\overset{\overset{O}{\|}}{\underset{N}{|}}\overset{}{\underset{=}{\diagdown}}\overset{N-R^1}{\underset{R^2}{|}} \quad (I)$$

Preparation examples for the compounds of the formula (I) (in Table 1, "D" stands for "decomposition on melting")

| Ex. No. | Q | $R^1$ | $R^2$ | $R^3$ | Physical Data |
|---|---|---|---|---|---|
| 135 | NH | $CH_3$ | $OC_2H_5$ | 2-(cyclopropyl-CO)-4-Cl-phenyl | M.p.: 129° C. (D) |
| 136 | NH | $CH_3$ | $OC_3H_7$-i | 2-$COC_2H_5$-4-Cl-phenyl | M.p.: 122° C. |
| 137 | NH | $CH_3$ | $OC_3H_7$-i | 2-(cyclopropyl-CO)-4-$C_2H_5$-phenyl | M.p.: 119° C. |
| 138 | NH | $CH_3$ | $OC_3H_7$-i | 2-$COC_2H_5$-4-$C_2H_5$-phenyl | M.p.: 148° C. |
| 139 | NH | $CH_3$ | $SC_2H_5$ | 2-$COC_2H_5$-4-F-phenyl | M.p.: 112° C. |
| 140 | NH | $CH_3$ | $SCH_3$ | 2-(cyclopropyl-CO)-4-$C_2H_5$-phenyl | M.p.: 136° C. |
| 141 | NH | $CH_3$ | $OC_3H_7$-i | 2-$COC_2H_5$-4-F-phenyl | M.p.: 122° C. |

TABLE 1-continued
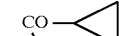
Preparation examples for the compounds of the formula (I) (in Table 1, "D" stands for "decomposition on melting")
| Ex. No. | Q | R¹ | R² | R³ | Physical Data |
|---|---|---|---|---|---|
| 142 | NH | $C_2H_5$ | $OCH_3$ | 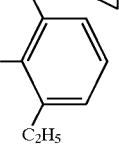 | M.p.: 131° C. |
| 143 | NH | $C_2H_5$ | $OCH_3$ | 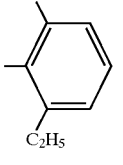 | M.p.: 107° C. |
| 144 | NH | $CH_3$ | $OC_3H_7$-i | 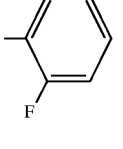 | M.p.: 137° C. |
| 145 | NH | $CH_3$ | $SCH_3$ | 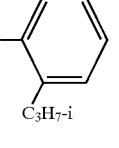 | M.p.: 139° C. |
| 146 | NH | $CH_3$ | $SCH_3$ | 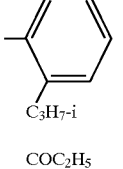 | M.p.: 146° C. |
| 147 | NH | $CH_3$ | $OC_3H_7$-i | 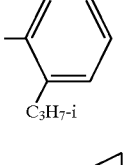 | M.p.: 131° C. |
| 148 | NH | $CH_3$ | $OC_2H_5$ | 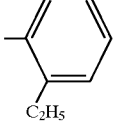 | M.p.: 98° C. |

TABLE 1-continued $$R^3-Q-SO_2-NH-CO-N\underset{N=\underset{R^2}{\overset{|}{\diagdown}}}{\overset{\overset{O}{\parallel}}{\diagup}}N-R^1 \quad (I)$$

Preparation examples for the compounds of the formula (I) (in Table 1, "D" stands for "decomposition on melting")

| Ex. No. | Q | R$^1$ | R$^2$ | R$^3$ | Physical Data |
|---|---|---|---|---|---|
| 149 | NH | CH$_3$ | OC$_2$H$_5$ | 2-COC$_2$H$_5$, 4-C$_2$H$_5$-phenyl | M.p.: 147° C. |
| 150 | NH | CH$_3$ | OC$_2$H$_5$ | 2-CO-cyclopropyl, 4-C$_3$H$_7$-i-phenyl | M.p.: 133 C. |
| 151 | NH | CH$_3$ | OC$_2$H$_5$ | 2-COC$_2$H$_5$, 4-C$_3$H$_7$-i-phenyl | M.p.: 123 C. |
| 152 | NH | C$_2$H$_5$ | OCH$_3$ | 2-CO-cyclopropyl, 4-C$_3$H$_7$-i-phenyl | M.p.: 159 C. |
| 153 | NH | C$_2$H$_5$ | OCH$_3$ | 2-COC$_2$H$_5$, 4-C$_3$H$_7$-i-phenyl | M.p.: 156 C. |
| 154 | NH | CH$_3$ | SC$_2$H$_5$ | 2-COC$_2$H$_5$, 4-C$_3$H$_7$-i-phenyl | M.p.: 121 C. |
| 155 | NH | CH$_3$ | SC$_2$H$_5$ | 2-CO-cyclopropyl, 4-C$_3$H$_7$-i-phenyl | M.p.: 130 C. |

TABLE 1-continued
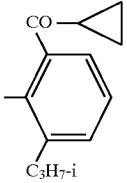
Preparation examples for the compounds of the formula (I) (in Table 1,
"D" stands for "decomposition on melting")
| Ex. No. | Q | R$^1$ | R$^2$ | R$^3$ | Physical Data |
|---|---|---|---|---|---|
| 156 | NH | CH$_3$ | N(CH$_3$)$_2$ | 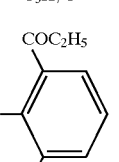 | M.p.: 145 C.(D) |
| 157 | NH | CH$_3$ | N(CH$_3$)$_2$ | 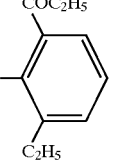 | M.p.: 131 C.(D) |
| 158 | NH | CH$_3$ | OCH$_2$CF$_3$ | 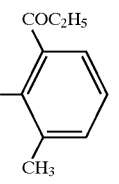 | M.p.: 134 C.(D) |
| 159 | NH | CH$_3$ | OCH$_2$CF$_3$ | 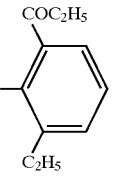 | M.p.: 124 C. |
| 160 | NH | CH$_3$ | OCH$_2$CF$_3$ | 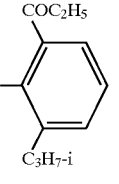 | M.p.: 85° C. |
| 161 | NH | CH$_3$ | OCH$_2$CF$_3$ | 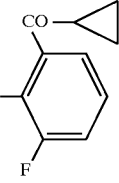 | M.p.: 89° C. |
| 162 | NH | CH$_3$ | OCH$_2$CF$_3$ | 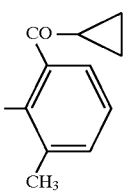 | M.p.: 127° C. |

TABLE 1-continued $$R^3-Q-SO_2-NH-CO-N\underset{N}{\overset{\underset{\displaystyle\|}{O}}{\underset{\|}{\overset{\displaystyle C}{}}}}\underset{R^2}{\overset{N-R^1}{}} \quad (I)$$

Preparation examples for the compounds of the formula (I) (in Table 1, "D" stands for "decomposition on melting")

| Ex. No. | Q | $R^1$ | $R^2$ | $R^3$ | Physical Data |
|---|---|---|---|---|---|
| 163 | NH | $CH_3$ | $OC_2H_5$ | 2-$COC_2H_5$, 4-$C_3H_7$-n phenyl | M.p.: 117° C. |
| 164 | NH | $-CH_2-CH=CH_2$ | $OCH_2CF_3$ | 2-(CO-cyclopropyl), 4-$C_2H_5$ phenyl | M.p.: 104° C. |
| 165 | NH | $-CH_2-CH=CH_2$ | $OCH_2CF_3$ | 2-$COC_2H_5$, 4-$C_3H_7$-i phenyl | M.p.: 133° C.(D) |
| 166 | NH | $-CH_2-CH=CH_2$ | $OCH_2CF_3$ | 2-(CO-cyclopropyl), 4-$CH_3$ phenyl | M.p.: 116° C. |
| 167 | NH | $-CH_2-CH=CH_2$ | $OCH_2CF_3$ | 2-$COC_2H_5$, 4-$CH_3$ phenyl | M.p.: 96° C.(D) |
| 168 | NH | $-CH_2-CH=CH_2$ | $OCH_2CF_3$ | 2-$COCH_3$, 4-$CH_3$ phenyl | M.p.: 119° C. |
| 169 | NH | $-CH_2-CH=CH_2$ | $OCH_2CF_3$ | 2-$COC_3H_7$-i, 4-$CH_3$ phenyl | M.p.: 99° C. |

TABLE 1-continued $$R^3-Q-SO_2-NH-CO-N\overset{\overset{O}{\|}}{\underset{N}{|}}\overset{}{\underset{=}{\diagdown}}\overset{N-R^1}{\underset{R^2}{}}\quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 170 | NH | CH₃ | OC₂H₅ | COC₂H₅–(phenyl with CH₃) | M.p.: 187° C. |
| 171 | NH | CH₃ | OC₂H₅ | COC₂H₅–(phenyl with CH₃) | (Syrup, Triethylammonium salt of No. 170) |
| 172 | NH | CH₃ | cyclopropyl | COC₂H₅–(phenyl with C₂H₅) | M.p.: 124° C. |
| 173 | NH | CH₃ | OC₃H₇-n | COC₂H₅–(phenyl with F) | M.p.: 132° C. |
| 174 | NH | CH₃ | OC₃H₇-n | CO-cyclopropyl–(phenyl with CH₃) | M.p.: 123° C. |
| 175 | NH | CH₃ | OC₃H₇-n | COC₂H₅–(phenyl with C₂H₅) | M.p.: 116° C. |
| 176 | NH | CH₃ | OC₃H₇-n | CO-cyclopropyl–(phenyl with C₃H₇-i) | M.p.: 137° C. |

TABLE 1-continued

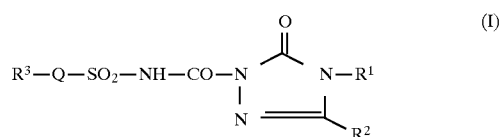

Preparation examples for the compounds of the formula (I) (in Table 1, "D" stands for "decomposition on melting")

| Ex. No. | Q | R¹ | R² | R³ | Physical Data |
|---|---|---|---|---|---|
| 177 | NH | $CH_3$ | $OC_3H_7$-n | $COC_2H_5$ on phenyl with $C_3H_7$-i | M.p.: 129° C. |
| 178 | NH | $CH_3$ | $OC_2H_5$ | $COC_3H_7$-i on phenyl with $CH_3$ | M.p.: 128° C. |
| 179 | NH | $CH_3$ | $OC_2H_5$ | $COCH_3$ on phenyl with $CH_3$ | M.p.: 128° C. |
| 180 | NH | $CH_3$ | $SCH_3$ | $COC_3H_7$-i on phenyl with $CH_3$ | M.p.: 129° C. |
| 181 | NH | $CH_3$ | $OC_3H_7$-n | $COC_2H_5$ on phenyl with $CH_3$ | M.p.: 118° C. |
| 182 | NH | $CH_3$ | $OC_3H_7$-n | $COC_3H_7$-i on phenyl with $CH_3$ | M.p.: 98° C. |
| 183 | NH | $CH_3$ | $OC_3H_7$-n | $COCH_3$ on phenyl with $CH_3$ | M.p.: 123° C. |

TABLE 1-continued $$R^3-Q-SO_2-NH-CO-N\overset{\displaystyle O}{\underset{N}{\underset{\parallel}{\bigg|}}}\overset{\displaystyle \|}{\underset{R^2}{C}}N-R^1 \quad (I)$$

Preparation examples for the compounds of the formula (I) (in Table 1, "D" stands for "decomposition on melting")

| Ex. No. | Q | $R^1$ | $R^2$ | $R^3$ | Physical Data |
|---|---|---|---|---|---|
| 184 | NH | $C_2H_5$ | $OCH_3$ | $COC_3H_7$-i, phenyl with $CH_3$ | M.p.: 125° C. |
| 185 | NH | $C_2H_5$ | $OCH_3$ | $COCH_3$, phenyl with $CH_3$ | M.p.: 125° C. |
| 186 | NH | cyclopropyl | $OC_3H_7$-n | $COC_2H_5$, phenyl with $CH_3$ | M.p.: 76° C. |
| 187 | NH | cyclopropyl | $OC_3H_7$-n | CO-cyclopropyl, phenyl with $C_3H_7$-i | M.p.: 113° C. |
| 188 | NH | cyclopropyl | $OC_3H_7$-n | $COC_2H_5$, phenyl with $C_3H_7$-i | M.p.: 115° C. |
| 189 | NH | cyclopropyl | $OC_3H_7$-n | $COCH_3$, phenyl with $CH_3$ | M.p.: 123° C. |
| 190 | NH | $N(CH_3)_2$ | $CH_3$ | $COC_2H_5$, phenyl with $CH_3$ | M.p.: 98° C. |

TABLE 1-continued $$R^3-Q-SO_2-NH-CO-N\begin{array}{c}O\\\parallel\\C\\|\\N\end{array}N-R^1 \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 191 | NH | CH₃ | OC₂H₅ | 2-COC₂H₅, 5-SCH₃-phenyl | M.p.: 131° C. |
| 192 | NH | CH₃ | SCH₃ | 2-COC₂H₅, 5-SCH₃-phenyl | M.p.: 118° C. |
| 193 | NH | CH₃ | OC₃H₇-i | 2-COC₂H₅, 5-SCH₃-phenyl | M.p.: 115° C. |
| 194 | NH | CH₃ | OC₃H₇-n | 2-COOC₂H₅, 5-CH₃-phenyl | |
| 195 | NH | CH₃ | OC₃H₇-i | 2-COOC₂H₅, 5-CH₃-phenyl | |
| 196 | NH | CH₃ | C₂H₅ | 2-COOCH₂CF₃, 5-CH₃-phenyl | |
| 197 | NH | CH₃ | OC₃H₇-n | 2-COOCH₂CF₃, 5-CH₃-phenyl | |

TABLE 1-continued $$R^3-Q-SO_2-NH-CO-N(CO)N-R^1, \quad N=R^2 \quad (I)$$

Preparation examples for the compounds of the formula (I) (in Table 1, "D" stands for "decomposition on melting")

| Ex. No. | Q | $R^1$ | $R^2$ | $R^3$ | Physical Data |
|---|---|---|---|---|---|
| 198 | NH | $CH_3$ | $OC_3H_7$-i | 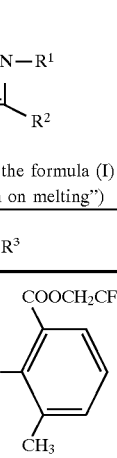 2-$COOCH_2CF_3$, 4-$CH_3$ phenyl | |
| 199 | NH | $CH_3$ | $SCH_3$ | 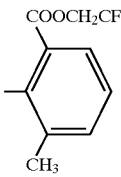 2-$COOCH_2CF_3$, 4-$CH_3$ phenyl | |
| 200 | NH | $CH_3$ | $OCH_3$ | 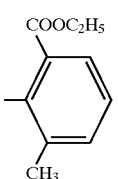 2-$COOC_2H_5$, 4-$CH_3$ phenyl | |
| 201 | NH | $CH_3$ | $SC_2H_5$ | 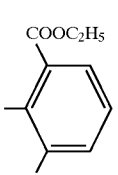 2-$COOC_2H_5$, 4-$CH_3$ phenyl | |
| 202 | NH | $CH_3$ | $SC_2H_5$ | 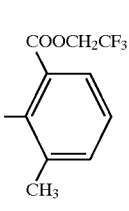 2-$COOCH_2CF_3$, 4-$CH_3$ phenyl | |
| 203 | NH |  cyclopropyl | $OC_2H_5$ | 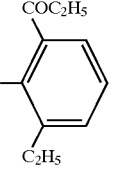 2-$COC_2H_5$, 4-$C_2H_5$ phenyl | M.p.: 92° C. |
| 204 | NH |  cyclopropyl | $OC_2H_5$ | 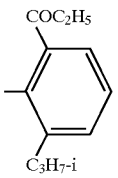 2-$COC_2H_5$, 4-$C_3H_7$-i phenyl | M.p.: 108° C. |

TABLE 1-continued $$R^3-Q-SO_2-NH-CO-N\underset{N}{\overset{\overset{\displaystyle O}{\|}}{\underset{\|}{C}}}\underset{R^2}{\overset{N-R^1}{=}} \quad (I)$$

Preparation examples for the compounds of the formula (I) (in Table 1, "D" stands for "decomposition on melting")

| Ex. No. | Q | R¹ | R² | R³ | Physical Data |
|---|---|---|---|---|---|
| 205 | NH |  | OC$_2$H$_5$ | 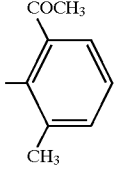 2-COCH$_3$, 6-CH$_3$ phenyl | M.p.: 132° C. |
| 206 | NH |  | OC$_2$H$_5$ | 2-COC$_3$H$_7$-i, 6-CH$_3$ phenyl | M.p.: 88° C. |
| 207 | NH | 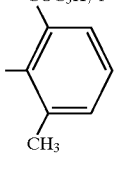 | OC$_2$H$_5$ | 2-COC$_2$H$_5$, 5-OCF$_3$ phenyl | M.p.: 135° C. |
| 208 | NH | CH$_3$ | C$_2$H$_5$ | 2-COC$_2$H$_5$, 5-OCF$_3$ phenyl | M.p.: 116° C. |
| 209 | NH | CH$_3$ | SC$_2$H$_5$ | 2-COC$_2$H$_5$, 5-OCF$_3$ phenyl | M.p.: 134° C. |
| 210 | NH | CH$_3$ | OC$_2$H$_5$ | 2-COC$_2$H$_5$, 5-OCF$_3$ phenyl | M.p.: 147° C. |
| 211 | NH | 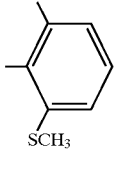 | OC$_2$H$_5$ | 2-COCH$_3$, 5-SCH$_3$ phenyl | M.p.: 95° C. |

TABLE 1-continued

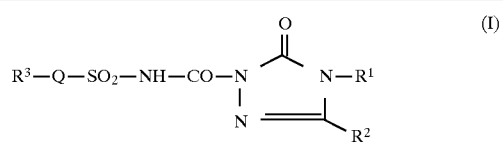

Preparation examples for the compounds of the formula (I) (in Table 1,
"D" stands for "decomposition on melting")

| Ex. No. | Q | R¹ | R² | R³ | Physical Data |
|---|---|---|---|---|---|
| 212 | NH | cyclopropyl | OC$_2$H$_5$ | 2-(cyclopropyl-CO)-4-OCF$_3$-phenyl | M.p.: 127° C. |
| 213 | NH | CH$_3$ | SCH$_3$ | 2-(cyclopropyl-CO)-4-OCF$_3$-phenyl | M.p.: 127° C. |
| 214 | NH | CH$_3$ | OCH$_3$ | 2-(cyclopropyl-CO)-4-OCF$_3$-phenyl | M.p.: 130° C. |
| 215 | NH | CH$_3$ | OC$_2$H$_5$ | 2-(cyclopropyl-CO)-4-OCF$_3$-phenyl | M.p.: 142° C. |
| 216 | NH | CH$_3$ | OCH$_3$ | 2-COOCH$_3$-4-CH$_3$-phenyl | M.p.: 168° C. |
| 217 | NH | CH$_3$ | OCH$_3$ | 2-OCHF$_2$-4-CH$_3$-phenyl | M.p.: 149° C. |
| 218 | NH | CH$_3$ | OCH$_3$ | 2-OCHF$_2$-5-CH$_3$-phenyl | M.p.: 130° C. |

TABLE 1-continued $$R^3-Q-SO_2-NH-CO-N\underset{N}{\overset{|}{\underset{\|}{\big|}}}\overset{O}{\underset{\|}{\text{C}}}\underset{R^2}{\overset{N-R^1}{\big\|}}\quad (I)$$

Preparation examples for the compounds of the formula (I) (in Table 1, "D" stands for "decomposition on melting")

| Ex. No. | Q | $R^1$ | $R^2$ | $R^3$ | Physical Data |
|---|---|---|---|---|---|
| 219 | NH | $CH_3$ | $SCH_3$ | $COOCH_3$, phenyl with $CH_3$ | M.p.: 151° C. |
| 220 | NH | $CH_3$ | $SCH_3$ | $OCHF_2$, phenyl with $CH_3$ | M.p.: 145° C. |
| 221 | NH | $CH_3$ | $SCH_3$ | $OCHF_2$, phenyl with $CH_3$ | M.p.: 156° C. |
| 222 | NH | $CH_3$ | $SC_2H_5$ | $COOCH_3$, phenyl with $CH_3$ | M.p.: 100° C. |
| 223 | NH | $CH_3$ | $SC_2H_5$ | $OCHF_2$, phenyl with $CH_3$ | M.p.: 138° C. |
| 224 | NH | $CH_3$ | $SC_2H_5$ | $OCHF_2$, phenyl with $CH_3$ | M.p.: 137° C. |
| 225 | NH | $CH_3$ | $C_2H_5$ | $COOCH_3$, phenyl with $CH_3$ | M.p.: 149° C. |
| 226 | NH | $CH_3$ | $C_2H_5$ | $OCHF_2$, phenyl with $CH_3$ | M.p.: 114° C. |

TABLE 1-continued

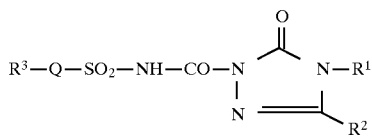

Preparation examples for the compounds of the formula (I) (in Table 1, "D" stands for "decomposition on melting")

| Ex. No. | Q | R¹ | R² | R³ | Physical Data |
|---|---|---|---|---|---|
| 227 | NH | CH₃ | Br | COOCH₃-(2,3-dimethylphenyl) | M.p.: 143° C. |
| 228 | NH | CH₃ | Br | OCHF₂-(3,4-dimethylphenyl) | M.p.: 135° C. |
| 229 | NH | cyclopropyl | SC₂H₅ | COOCH₃-(2,3-dimethylphenyl) | M.p.: 124° C. |
| 230 | NH | cyclopropyl | SC₂H₅ | OCHF₂-(3,4-dimethylphenyl) | M.p.: 110° C. |
| 231 | NH | cyclopropyl | Br | COOCH₃-(2,3-dimethylphenyl) | M.p.: 108° C. |
| 232 | NH | cyclopropyl | Br | OCHF₂-(3,4-dimethylphenyl) | M.p.: 144° C. |
| 233 | NH | CH₃ | OC₂H₅ | COOCH₃-(2,3-dimethylphenyl) | M.p.: 139° C. |

TABLE 1-continued

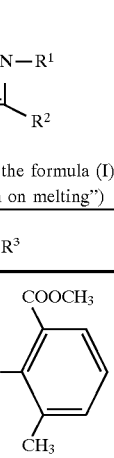
(I)

Preparation examples for the compounds of the formula (I) (in Table 1, "D" stands for "decomposition on melting")

| Ex. No. | Q | R¹ | R² | R³ | Physical Data |
|---|---|---|---|---|---|
| 234 | NH | CH$_3$ | OC$_3$H$_7$-n | COOCH$_3$ / CH$_3$ (phenyl) | M.p.: 124° C. |
| 235 | NH | CH$_3$ | OC$_4$H$_9$-s | COOCH$_3$ / CH$_3$ (phenyl) | M.p.: 121° C. |
| 236 | NH | CH$_3$ | OCH$_2$-cyclopropyl | COOCH$_3$ / CH$_3$ (phenyl) | M.p.: 130° C. |
| 237 | NH | CH$_3$ | OCH$_2$CF$_3$ | COOCH$_3$ / CH$_3$ (phenyl) | M.p.: 136° C. |
| 238 | NH | CH$_3$ | SCH$_2$CF$_3$ | COOCH$_3$ / CH$_3$ (phenyl) | M.p.: 139° C. |
| 239 | NH | CH$_3$ | SCH$_2$CH$_2$F | COOCH$_3$ / CH$_3$ (phenyl) | M.p.: 141° C. |
| 240 | NH | CH$_3$ | C$_3$H$_7$-n | COOCH$_3$ / CH$_3$ (phenyl) | M.p.: 137° C. |

TABLE 1-continued $$R^3-Q-SO_2-NH-CO-N\overset{\overset{O}{\|}}{\underset{N}{\phantom{|}}}\!\!\!\underset{}{}\!\!\!\overset{}{}\!\!\!N-R^1 \quad (I)$$

with the ring: N—N=C(R²)

Preparation examples for the compounds of the formula (I) (in Table 1, "D" stands for "decomposition on melting")

| Ex. No. | Q | R¹ | R² | R³ | Physical Data |
|---|---|---|---|---|---|
| 241 | NH | CH₃ | cyclopropyl | 2-COOCH₃-4-CH₃-phenyl | M.p.: 151° C. |
| 242 | NH | CH₃ | OC₃H₇-i | 2-COOCH₃-4-CH₃-phenyl | M.p.: 148° C. |
| 243 | NH | cyclopropyl | OCH₃ | 2-COOCH₃-4-CH₃-phenyl | M.p.: 140° C. |
| 244 | NH | cyclopropyl | OC₃H₇-n | 2-COOCH₃-4-CH₃-phenyl | M.p.: 134° C. |
| 245 | NH | cyclopropyl | OC₃H₇-i | 2-COOCH₃-4-CH₃-phenyl | M.p.: 142° C. |

Starting compounds of the formula (II)

Example (II-1)

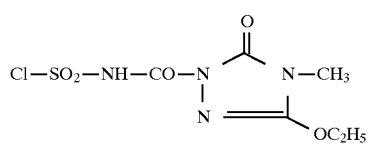

28.8 g (0.20 mol) of 5-ethoxy-4-methyl-2,4-dihydro-3H-1,2,-triazol-3-one are initially introduced into 250 ml of methylene chloride, and the mixture is cooled down to −10° C. 28.3 g (0.20 mol) of chlorosulphonyl isocyanate are added, and the reaction mixture is stirred for 30 minutes without cooling. The solvent is then carefully distilled off under a water pump vacuum.

53 g (93% of theory) of 2-chlorosulphonylaminocarbonyl-5-ethoxy-4-methyl-2,4-dihydro-3H-1,2,-triazol-3-one are obtained as a crystalline residue with a melting point of 106° C.

Example (II-2)

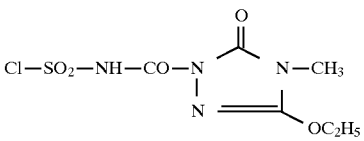

22.6 g (0.20 mol) of 4,5-dimethyl-2,4dihydro-3H-1,2,4-triazol-3-one are initially introduced into 250 ml of methylene chloride, and the mixture is cooled down to −10° C. 28.3 g (0.20 mol) of chlorosulphonyl isocyanate are then added and the mixture is stirred at from −5° C. to −10° C.

for 20 minutes, with a clear solution being formed initially and the product then separating out in crystalline form It is isolated by filtering it off with suction.

45 g (88% of theory) of 2-chlorosulphonylaminocarbonyl4,5-dimethyl-2,4dihydro-3H- 1,2,4-triazol-3-one are obtained with a melting point of 150° C. (with decomposition).

Example (II-3)

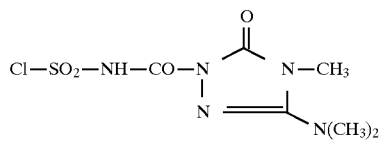

9.9 g (72 mmol) of chlorosulphonyl isocyanate are added slowly, at from −10° C. to 0° C., to 10 g (72 mmol) of 5-dimethylamino-4-methyl-2,4-dihydro-3H-1,2,4-triazol-3-one in 250 ml of methylene chloride. After it has been stirred for 30 minutes, the reaction mixture has reached room temperature (20° C.). The solvent is then removed by distillation under a water pump vacuum.

19.1 g (94% of theory) of 2-chlorosulphonylaminocarbonyl-5-dimethylamino-4-methyl-2,4-dihydro-3H-1,2,-triazol-3-one are obtained as an amorphous residue.

Starting compounds of the formula (III)

Exeampl (III-1)

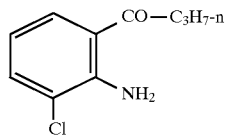

32.0 g (0.25 mol) of 2-chloro-aniline are added, while cooling with ice, to a solution of 33.8 g (0.29 mol) of boron(II) chloride in 200 ml of dichloroehane. 22.0 g (0.32 mol) of butyronitrile and 38 g (0.28 mol) of aluminum chloride are then added in succession at 0° C. The mixture is heated under reflux for 15 hours and, after having cooled down, is poured onto ice water, the organic phase is then separated off, dried with sodium sulphate and distilled.

12 g (24% of theory) of 2-chloro-6-propylcarbonyl-aniline are obtained with a boiling point of 105° C. (2 mbar).

Example (III-2)

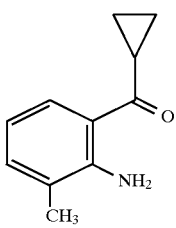

30 g (0.25 mol) of boron(III) chloride are added, at from 0° C. to +5° C., to 250 ml of dichloroehane, and 26.8 g (0.25 mol) of 2-methyl-aniline are added dropwise, at from 0° C. to +5° C., to this mixture. 25 g (0.375 mol) of cyclopropyl cyanide are then added dropwise at from 0° C. to +5° C., followed by 36 g (0.275 mol) of aluminum(III) chloride, which is metered in in portions. The reaction mixture is then heated under reflux for approx 15 hours, after which it is allowed to cool and is then poured onto approx. 1 litre of ice water. This mixture is stirred until the solid components have; dissolved, after which the organic phase is separated oft dried with sodium sulphate and filtered. The filtrate is concentrated under a water pump vacuum, the residue is caused to crystallize by digesting it with ligroin, and the product is isolated by filtering it off with suction.

58 g (66% of theory) of 2-cyclopropylcarbonyl-6-methyl-aniline are obtained with a melting point of 64° C.

APPLICATION EXAMPLES

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound. It is expedient to keep constant the amount of water per unit area The concentration of the active compound in the preparation is of no importance, only the amount of active compound applied per unit area being decisive. After three weeks, the degree of damage to the plants is rated in % damage in comparison to, the development of the untreated control. The figures denote:

0%=no effect (like untreated control)
100%=total destruction

The tested active compounds, the quantities in which they are applied, the test plants and the test results which are obtained are shown in Table A below.

In Table A, the numbers of the active compounds refer to the above-described preparation examples (cf. Example 1 and Table 1).

TABLE A

| | | Pre-emergence test/greenhouse | | | | | | |
|---|---|---|---|---|---|---|---|---|
| Active compound No. | Quantity applied (kg/ha) | Wheat | Maize | Galium | Galinsoga | Portulaca | Sinapis | Solanum |
| 1 | 125 | 0 | 80 | 100 | 100 | 95 | 95 | 95 |
| 23 | 30 | 0 | 0 | 95 | 95 | 95 | 95 | 90 |
| 24 | 60 | 0 | 40 | 95 | 95 | 95 | 95 | 95 |

TABLE A-continued

Pre-emergence test/greenhouse

| Active compound No. | Quantity applied (kg/ha) | Wheat | Maize | Galium | Galinsoga | Portulaca | Sinapis | Solanum |
|---|---|---|---|---|---|---|---|---|
| 36 | 125 | 0 | 50 | 70 | 100 | 95 | 90 | 90 |
| 103 | 125 | 0 | 0 | 95 | 100 | 70 | 90 | 95 |
| 108 | 125 | 0 | 0 | 95 | 95 | 80 | 80 | 95 |
| 111 | 250 | 0 | 0 | 95 | 95 | 95 | 95 | 95 |
| 114 | 125 | 0 | 10 | 95 | 95 | 90 | 95 | 95 |
| 118 | 125 | 0 | 0 | 95 | 95 | 80 | 90 | 95 |
| 132 | 125 | 0 | 0 | 90 | 95 | 60 | 95 | 95 |
| 134 | 125 | 0 | 0 | 95 | 95 | 80 | 95 | 95 |
| 135 | 60 | 20 | 0 | 80 | 95 | 70 | 80 | 60 |
| 138 | 250 | 0 | 40 | 95 | 95 | 95 | 80 | 95 |
| 141 | 125 | 0 | 0 | 80 | 70 | 90 | 80 | 90 |
| 143 | 125 | 20 | 0 | 70 | 95 | 90 | 70 | 90 |
| 148 | 30 | 0 | 30 | 80 | 95 | 95 | 90 | 95 |
| 174 | 125 | 0 | 10 | 70 | 90 | 80 | 90 | 90 |
| 204 | 125 | 30 | 0 | 95 | 95 | 95 | 95 | 95 |
| 206 | 125 | 0 | 0 | 90 | 100 | 95 | 95 | 95 |
| 216 | 30 | 0 | 60 | 90 | 95 | 50 | 90 | 90 |

Example B

Post-emergence test

Solvent: 5 parts by weight of acetone
Emulsifier: 1 par t by weight of alkylaryl polyglycol ether To produce a suitable preparation of active compound, 1 part by weight of active compound is mixed with the stated amount of solvent the stated amount of emulsifier is added and the concentrate is diluted with water to the desired concentration.

Test plants which have a height of 5–15 cm are spayed wit h the preparation of the active compound in such a way as to apply the particular amounts of active compound desired per unit area. The concentration of the spray liquor is chosen such that the, particular amounts of active compound desired are applied in 2,000 1 of water/ha. After three weeks, the degree of damage to the plants is rated in % damage in comparison to the development of the untreated control.

The figures denote:

0%=no effect (like untreated control)
100%=total destruction

The tested active compounds, the quantities in which they are applied, the test plants and the test results which are obtained are shown in Table B below.

In Table B, the numbers of the active compounds refer to the above preparation examples.

TABLE B

Post-emergence test/greenhouse

| Active compound No. | Quantity applied (kg/ha) | Wheat | Maize | Amaranthus | Galium | Ipomoea | Polygonum | Solanum |
|---|---|---|---|---|---|---|---|---|
| 103 | 60 | 0 | 15 | 70 | 95 | 60 | 70 | 95 |
| 108 | 125 | 0 | 50 | 80 | 95 | 70 | 90 | 95 |
| 120 | 60 | 0 | 10 | 90 | 40 | 70 | 90 | 90 |
| 123 | 30 | 0 | 40 | 95 | 90 | 95 | 90 | 90 |
| 124 | 60 | 0 | 5 | 80 | 90 | 100 | 20 | 90 |
| 126 | 60 | 0 | 5 | 40 | 60 | 90 | 30 | 90 |
| 131 | 125 | 0 | 10 | 90 | 70 | 40 | 60 | 80 |
| 132 | 125 | 0 | 5 | 95 | 90 | 95 | 50 | 100 |
| 134 | 125 | 0 | 0 | 95 | 90 | 95 | 80 | 100 |
| 174 | 30 | 0 | 0 | 100 | 95 | 95 | 50 | 95 |
| 216 | 15 | 0 | 70 | 100 | 80 | 70 | 80 | 95 |
| 229 | 125 | 0 | 15 | 90 | 80 | 95 | 60 | 70 |

We claim:

1. A sulphonylaminocarbonyltriazolinone of the formula

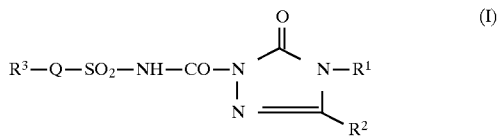
(I)

in which

Q represents —NH—, $R^1$ represents hydrogen, $C_1$–$C_6$-alkyl or $C_3$–$C_6$-cycloalkyl;

$R^2$ represents $C_1$–$C_6$-alkoxy;

$R^3$ represents phenyl which is substituted at least twice by $C_1$–$C_4$-alkyl, $C_1$–$C_4$-alkylcarbonyl, $C_3$–$C_6$- cycloalkylcarbonyl, or $C_1$–$C_4$-alkoxycarbonyl where one of the substituents is different from alkyl, or a salt thereof.

2. The compound according to claim 1, wherein $R^1$ represents methyl or cyclopropyl;

$R^2$ represents methoxy or ethoxy, $R^3$ represents a phenyl group which is substituted at least twice by methyl, ethylcarbonyl, cyclopropylcarbonyl, or methoxycarbonyl and at least one of the substituents is different from methyl.

3. The compound according to claim 1, wherein the salt is the sodium, potassium, magnesium, calcium, ammonium, $C_1$–$C_4$-alkylammonium, di-($C_1$–$C_4$-alkyl)-ammonium, tri($C_1$–$C_4$-alkyl)ammonium, $C_5$- or $C_6$-cycloalkyl-ammonium and di-$C_1$–$C_2$-alkyl)-benzyl-ammonium salt.

4. The compound according to claim 1, which is

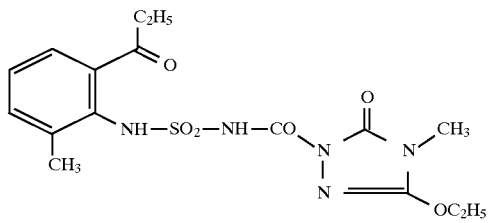

or a salt thereof.

5. The compound according to claim 1, which is

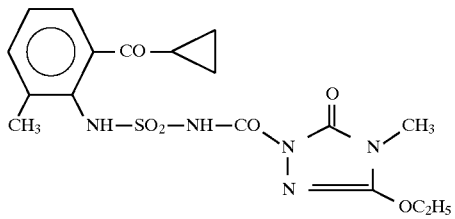

or a salt thereof.

6. A herbicidal composition which comprises an effective amount of a compound according to claim 1 and an inert carrier.

7. A method for controlling weeds which comprises applying herbicidally effective amount of a compound according to claim 1 to said weeds or to a habitat to which they reside.

* * * * *